(12) United States Patent
Zeng et al.

(10) Patent No.: US 11,052,099 B2
(45) Date of Patent: Jul. 6, 2021

(54) USE OF CIMICIFUGAE RHIZOMA TRITERPENOID SAPONIN EXTRACT, ACTEIN, AND DEOXYACTEIN

(71) Applicant: BEIJING DITAN HOSPITAL, CAPITAL MEDICAL UNIVERSITY, Beijing (CN)

(72) Inventors: Hui Zeng, Beijing (CN); Xianbo Wang, Beijing (CN); Liuluan Zhu, Beijing (CN); Rui Li, Beijing (CN)

(73) Assignee: BEIJING DITAN HOSPITAL, CAPITAL MEDICAL UNIVERSITY, Beijing (CN)

( * ) Notice: Subject to any disclaimer, the term of this patent is extended or adjusted under 35 U.S.C. 154(b) by 0 days.

(21) Appl. No.: 16/621,949

(22) PCT Filed: Jun. 13, 2018

(86) PCT No.: PCT/CN2018/091057
§ 371 (c)(1),
(2) Date: Dec. 12, 2019

(87) PCT Pub. No.: WO2018/228431
PCT Pub. Date: Dec. 20, 2018

(65) Prior Publication Data
US 2020/0108087 A1    Apr. 9, 2020

(30) Foreign Application Priority Data
Jun. 13, 2017   (CN) .......................... 201710445157.9

(51) Int. Cl.
*A61K 31/7048* (2006.01)
(52) U.S. Cl.
CPC ............................... *A61K 31/7048* (2013.01)
(58) Field of Classification Search
CPC .................................................. A61K 31/7048
See application file for complete search history.

(56) References Cited

U.S. PATENT DOCUMENTS

2013/0177627 A1    7/2013  Einbond et al.

FOREIGN PATENT DOCUMENTS

| CN | 1634311 | 7/2005 |
| CN | 102348668 | 2/2012 |
| CN | 105055738 | 11/2015 |

OTHER PUBLICATIONS

Einbond et al., Planta Med., 2006, 76, p. 1200-1206, supporting information p. 3292-e297. (Year: 2006).*

Kong L et al: "Analysis of terpene compounds in *Cimicifuga foetida* L. by reversed-phase high-performance liquid chromatography with evaporative light scattering detection", Journal of Chromatography A, Elsevier, Amsterdam, NL, vol. 936, No. 1-2, Nov. 30, 2001 (Nov. 30, 2001), pp. 111-118, XP004322047.
Desong Wu et al: "The in Vitro and in Vivo Antitumor Activities of Tetracyclic Triterpenoids Compounds Actein and 26-Deoxyactein Isolated from Rhizome of *Cimicifuga foetida* L.", Molecules Online, vol. 21, No. 8, Jan. 1, 2016 (Jan. 1, 2016), p. 1001, XP055679133.
Linda Saxe Einbond et al: "Growth Inhibitory Activity of Extracts and Purified Components of Black Cohost on Human Breast Cancer Cells", Breast Cancer Research and Treatment, Springer , NY, US, vol. 83, No. 3, Feb. 3, 2004 (Feb. 3, 2004), pp. 221-231, XP008037556.
Einbond L S et al: "Growth inhibitory activity of extracts and compounds from Cimicifuga species on human breast cancer cells", Phytomedicine, Elsevier, Amsterdam, NL, vol. 15, No. 6-7, Jun. 20, 2008 (Jun. 20, 2008), pp. 504-511, XP022711348.
He K et al: "Direct Analysis and Identification of Triterpene GL Ycosides by LC/MS in Black. Cohosh, Cimicifuga Racemosa, and in Several Commercially Available Black Cohosh Products", Planta Medica, Thieme Verlag, DE, vol. 66, No. 7, Oct. 1, 2000 (Oct. 1, 2000), pp. 635-640, XP009046315.
Edward Sauter et al: "Black Cohosh: Insights into its Mechanism(s) of Action",Integrative Medicine Insights, Jan. 1, 2008 (Jan. 1, 2008), pp. 3-21, XP55679308, Retrieved from the Internet: URL:https://www.ncbi.nlm.nih.gov/pmc/articles/PMC3046019/pdf/imi-2008-021.pdf [retrieved on Mar. 24, 2020].
Avula Bharathi et al: "Quantitative Determination of Triterpenoids and Formononetin in Rhizomes of Black Cohosh (*Actaea racemosa*) and Dietary Supplements by Using UPLC-UV/ELS Detection and Identification by UPLC-MS", Planta Medica, Thieme Verlag, DE, vol. 75, No. 4 Mar. 1, 2009 (Mar. 1, 2009), pp. 381-386, XP009165926.
Chen, NA et al.: "Protective Effect of Prim-o-glucosyl-cimifugin on LPSinduced Lung Injury Model in Mice", 2013 Twelfth Academic Symposium of Veterinary Pharmacology and Toxicology Branch of Chinese Society of Animal Husbandry and Veterinary Medicine, Sep. 1, 2014 (Sep. 1, 2014), p. 122, XP009518580.
Chen, Na et al. "Protective Effect of Prim-o-glucosyl-cimifugin on LPS-induced Lung Injury Model in Mice (Non-official translation)"; Proceedings of the Twelfth Symposium on Veterinarian Pharma-Toxicology Branch of Chinese Association of Animal Science and Veterinary Medicine (Non-official translation). Sep. 1, 2014 (Sep. 1, 2014).

* cited by examiner

*Primary Examiner* — Jonathan S Lau
(74) *Attorney, Agent, or Firm* — Hsuanyeh Law Group PC

(57) ABSTRACT

The present invention provides the use of *Cimicifugae rhizoma* triterpenoid saponin extract, *Cimicifugae rhizoma*, actein, deoxyactein, or a composition formed by actein and deoxyactein in the preparation of a medicament or a functional health product for autoimmune diseases. The present invention also provides a pharmaceutical composition for autoimmune diseases and a pharmaceutical composition for inhibiting inflammatory cytokines. The invention provides new applications of *Cimicifugae rhizoma* triterpenoid saponin extract, *Cimicifugae rhizoma*, actein, deoxyactein, etc., and widens the application field of medicines or functional health products for autoimmune diseases. The raw materials source is plenty, the cost is low, and it has a broad market application value.

3 Claims, 2 Drawing Sheets

USE OF CIMICIFUGAE RHIZOMA TRITERPENOID SAPONIN EXTRACT, ACTEIN, AND DEOXYACTEIN

TECHNICAL FIELD

The present invention relates to the field of medicine, in particular to the use of *Cimicifugae rhizoma* triterpenoid saponin extract, *Cimicifugae rhizoma*, actein, deoxyactein, or a composition formed by actein and deoxyactein in the preparation of medicine or functional health supplement for autoimmune diseases.

BACKGROUND OF THE INVENTION

The abnormal activation of innate immune cells and adaptive immune cells is the key pathogenesis of autoimmune diseases. Typical diseases are represented by autoimmune hepatitis and rheumatoid arthritis. Autoimmune hepatitis is a chronic progressive liver inflammatory disease mediated by an autoimmune response. It is characterized by elevated serum transaminase levels and positive autoantibodies. The histological features are impaired liver function and immune disorders caused by interface hepatitis characterized mainly by the infiltration of lymphocytes and plasma cells. Rheumatoid arthritis is a systemic disease mainly composed of inflammatory synovitis, which is characterized by polyarticular, symmetrical, and invasive arthritis of the small joints of the hands and feet, often accompanied by a rise in serum rheumatoid factor and inflammatory cytokines, and can cause joint deformities and loss of function. The development of new drugs or health products from the perspective of regulating the body's immunity is an important breakthrough in the treatment of autoimmune diseases, and the development of immune-modulating drugs or functional health products from the traditional medical resources of the motherland has broad prospects.

*Cimicifugae rhizoma* is from Cimicifuga of Ranunculaceae. Triterpenoid saponin extracts are prepared by extracting rhizomes and aerial parts of *Cimicifugae rhizoma*, which are generally believed to have various physiological activities such as anti-tumor, regulating endocrine, anti-osteoporosis, etc. It is a kind of natural products with great development prospects.

SUMMARY OF THE INVENTION

One of the objectives of the present invention is to provide new uses of a *Cimicifugae rhizoma* triterpenoid saponin extract, *Cimicifugae rhizoma*, actein, deoxyactein (also known as 27-deoxyactein), or a composition formed by actein and deoxyactein.

The present invention provides uses of a *Cimicifugae rhizoma* triterpenoid saponin extract, *Cimicifugae rhizoma*, actein, deoxyactein, or a composition formed by actein and deoxyactein in the preparation of a medicament or functional health product for autoimmune diseases.

In the above application, the autoimmune disease is autoimmune hepatitis or rheumatoid arthritis.

The present invention also provides uses of *Cimicifugae rhizoma* triterpenoid saponin extract, *Cimicifugae rhizoma*, actein, deoxyactein, or a composition formed by actein and deoxyactein for the preparation of a medicament or functional product for the inhibition of inflammatory cytokines.

In the above application, the inflammatory cytokines may include one or more of the following: TNF-α, IFN-γ, IL-6, IL-9, IL-12, IL-17A, IL-18, IP-10, MCP-1, MCP-3, MIP-1α, MIP-1β, MIP-2, Eotaxin, and G-CSF.

In the above application, the inflammatory cytokines may be involved in a variety of diseases caused by bacterial and viral infections, such as hepatitis, pneumonia, sepsis, influenza, measles, herpes simplex, etc.; they may also be involved in a variety of autoimmune diseases, such as rheumatoid arthritis, systemic vasculitis, scleroderma, multiple encephalomyelitis, etc. *Cimicifugae rhizoma* triterpenoid saponin extract, *Cimicifugae rhizoma*, actein, deoxyactein, or a composition formed by actein and deoxyactein can all be used as medicines or functional health products for preventing, alleviating and treating the above diseases.

In the above-mentioned application, the mass ratio of actein and deoxyactein in the composition formed by actein and deoxyactein, may be 1 to 5:5 to 1; preferably 1 to 3:3 to 1; more preferably 1:1.

In the above application, the medicament can have *Cimicifugae rhizoma* triterpenoid saponin extract, *Cimicifugae rhizoma*, actein, deoxyactein, or a composition formed by actein and deoxyactein as an active ingredient, and additionally, the medicament can contain a pharmaceutically acceptable carrier. Pharmaceutically acceptable carriers include, but are not limited to, excipients, binders, lubricants, fillers, disintegrants, emulsifiers, stabilizers, colorants, flavoring agents, preservatives, and the like. The medicine can be prepared into any common dosage form in the existing pharmaceutical field, including, but not limited to, oral dosage forms such as tablets, capsules, granules, pills, and non-oral dosage forms such as injections, lyophilizates, etc.

In the above-mentioned application, the functional health product can have *Cimicifugae rhizoma* triterpenoid saponin extract, *Cimicifugae rhizoma*, actein, deoxyactein, or a composition formed by actein and deoxyactein as an active ingredient, and common ingredients can be added to the functional health product. The common ingredients include but not limited to nutrients, vitamins, minerals, flavors, colorants, tackifiers, pH adjusters, stabilizers, preservatives, etc. The functional health products can be consumed alone or used in combination with existing medicines or health products.

Another object of the present invention is to provide a pharmaceutical composition.

The pharmaceutical composition provided by the present invention may be a pharmaceutical composition for autoimmune diseases. The pharmaceutical composition includes the following ingredients as active ingredients: *Cimicifugae rhizoma* triterpenoid saponin extract, *Cimicifugae rhizoma*, actein, deoxyactein, or a composition formed by actein and deoxyactein.

In the above pharmaceutical composition, the autoimmune disease is autoimmune hepatitis or rheumatoid arthritis.

The pharmaceutical composition provided by the present invention may also be a pharmaceutical composition for inhibiting inflammatory cytokines. The pharmaceutical composition contains the following ingredients as active ingredients: *Cimicifugae rhizoma* triterpenoid saponin extract, *Cimicifugae rhizoma*, actein, deoxyactein, or a composition formed by actein and deoxyactein.

In the above pharmaceutical composition, the inflammatory cytokines may include one or more of the following: TNF-α, IFN-γ, IL-6, IL-9, IL-12, IL-17A, IL-18, IP-10, MCP-1, MCP-3, MIP-1α, MIP-1β, MIP-2, Eotaxin, and G-CSF.

In the above-mentioned pharmaceutical composition, the mass ratio of actein and deoxyactein in the composition formed by actein and deoxyactein may be 1 to 5:5 to 1; preferably 1 to 3:3 to 1; more preferably 1:1.

The above pharmaceutical composition may further include a pharmaceutically acceptable carrier in addition to the active ingredient, including but not limited to excipients, binders, lubricants, fillers, disintegrants, emulsifiers, stabilizers, coloring agents, flavoring agents, preservatives, etc. The pharmaceutical composition can be administered alone or in combination with existing drugs for autoimmune diseases, and can be prepared into any common dosage form in the existing pharmaceutical field, including but not limited to oral dosage such as tablets, capsules, granules, and pills, and non-oral dosage forms such as injections and lyophilizates.

Among the above pharmaceutical compositions, the pharmaceutical composition may also be a Chinese medicinal composition including *Cimicifugae rhizoma*, for example, it may be a compatible medicine formed by *Cimicifugae rhizoma* and other Chinese medicinal ingredients, such as *Angelicae sinensis radix, Bupleuri radix, Citri Reticulatae pericarpium* and the like. The Chinese medicine composition can be administered alone or in combination with existing drugs for autoimmune diseases, and can be prepared into any common dosage form in the existing field of Chinese medicine, including but not limited to decoctions, liquors, tea, lotion, pill, powder, ointment, elixir, tablet, lozenge and so on.

In the present invention, through an animal model experiment of Concanavalin A (ConA), it is found that: *Cimicifugae rhizoma* triterpenoid saponin extract, *Cimicifugae rhizoma*, actein, deoxyactein, or its composition or pharmaceutical composition can protect against acute immune liver injury caused by ConA and can significantly improve the survival rate, liver function level, liver pathological damage and inflammatory cytokine secretion levels in animal models of autoimmune hepatitis, indicating that it can be used to prepare medicaments or health products to relieve autoimmune hepatitis.

The present invention also shows through experiments on animal models of collagen-induced arthritis (CIA) that actein, deoxyactein, *Cimicifugae rhizoma* triterpenoid saponin extract, *Cimicifugae rhizoma* or its composition and pharmaceutical composition has a protective effect on multiple joint injuries caused by CIA, and can significantly reduce the incidence of disease and the average index of arthritis in CIA animal models, and can improve the destruction of bone structure, reduce the secretion of anti-type II collagen antibodies and a variety of inflammatory cytokines. It has an exact anti-arthritis effect and can be used to prepare medicines or health products for treating or alleviating the symptoms of rheumatoid arthritis.

The present invention also finds through LPS-stimulated macrophages (BMDM) that *Cimicifugae rhizoma* triterpenoid saponin extract, *Cimicifugae rhizoma*, actein, deoxyactein or its composition, pharmaceutical composition and the like have exact anti-inflammatory effects, can significantly inhibit the activation of macrophages and the secretion of inflammatory cytokines such as IL-12, TNF-α, and in vitro experiments have found that it can also significantly inhibit the activation of NK, NKT and T lymphocytes and secretion of inflammatory cytokines. Therefore, it can also be used as an immunosuppressant to treat or improve diseases such as inflammation caused by various inflammatory cytokines.

In summary, the present invention provides new uses of *Cimicifugae rhizoma* triterpenoid saponin extracts, actein, and deoxyactein, and because of its extensive immunosuppressive effect, it develops the technical field of drugs or functional health products for autoimmune diseases. These ingredients can not only be produced by chemical synthesis or extraction, but also can directly use *Cimicifugae rhizoma* extract or Chinese compatibility medicines containing *Cimicifugae rhizoma*, which is easy to prepare, has a wide range of raw materials, low cost, and has a wide range of market application value.

EMBODIMENTS

Figure 1:
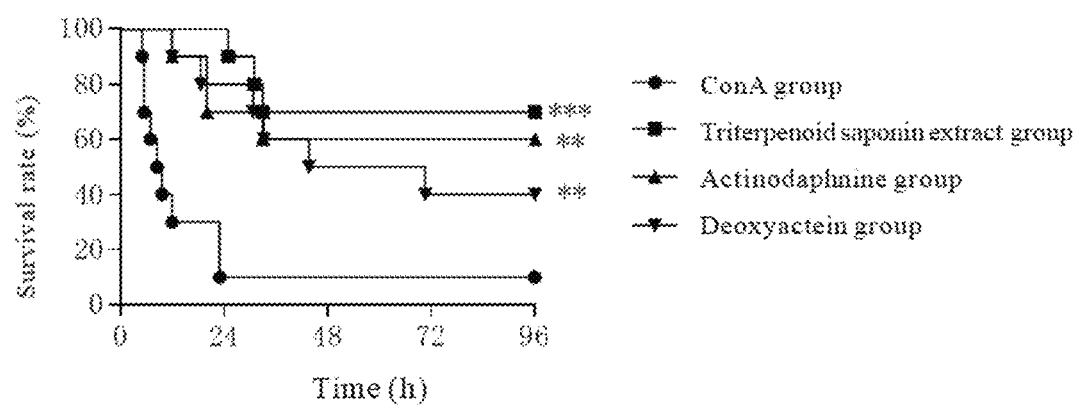
FIG. 1 is a survival rate chart of mice in each group in Experimental Example 1.

In the following, the present invention is described in detail through preparation examples and experimental examples to make the features and advantages of the present invention clearer. However, it should be noted that the Preparation Examples and Experimental Examples are used to understand the concept of the present invention, and the scope of the present invention is not limited to the preparation examples and experimental examples listed herein.

Unless otherwise specified, the experimental methods used in the following Preparation Examples and Experimental Examples are conventional methods. The materials and reagents used can be obtained from commercial sources unless otherwise specified.

Preparation Example. Preparation of *Cimicifugae rhizoma* Triterpenoid Saponin Extract

*Cimicifugae rhizoma* was purchased from Tongrentang Qianmen Head Office. Triterpenoid saponin was extracted based on the reference (Pan Ruile, Chen Dihua, Si Jianyong, Zhao Xiaohong, Shen Liangang. Study on saponin components of *Cimicifugae rhizoma* above ground. Pharmaceutical Journal. 2002, 37 (2): 117-120).

12 g of *Cimicifugae rhizoma* was immersed in distilled water for 1 to 2 h. Decocting for 10 minutes with high heat and then gently for 1 h. Concentrate the decoction to 75 mL. Took the 75 mL of *Cimicifugae rhizoma* decoction, added 95% ethanol to 1000 mL, precipitated overnight, and separated the supernatant. The supernatant was distilled under reduced pressure to sufficiently remove ethanol and excess water and concentrated to 75 mL to obtain a *Cimicifugae rhizoma* alcohol extract. At room temperature, organic solvent ethyl acetate was used to extract 5 times, stirred, extracted, and centrifuged to obtain the supernatant, and then extracted with 5% sodium carbonate. After recovering ethyl acetate under reduced pressure, a *Cimicifugae rhizoma* triterpenoid saponin extract was obtained. Then dissolved the extract in water to make 75 mL.

Experimental Example 1. Effect of Survival Rate of ConA Hepatitis Mouse Model

Test materials: ConA was purchased from Sigma; actein and deoxyactein were purchased from ChromaDex, USA.

Animal: C57BL/6 mice, purchased from Beijing Huafukang Biotechnology Co., Ltd.

Grouping: 40 C57BL/6 mice, male, 18-20 g, after 1 day of adaptive breeding, mice were randomly divided into 4 groups of 10 animals in each group: ConA model group, triterpenoid saponin group, actein group, and deoxyactein group.

Model preparation and drug administration: weighed 150 mg of ConA powder, dissolved it in 40 mL of sterile PBS, left it at room temperature for 1 to 2 hours, and continued to gently shake intermittently to mix well. Low temperature ultrasound was used to improve dissolution (no more than 5 min each time) and avoided excessive foaming. After it was fully dissolved, the volume was adjusted to 50 mL to a concentration of 3 mg/mL and filtered the solution under pressure with a 0.45 μm filter. Mice were given a single intravenous injection at 25 mg/kg, with 100 μL per mouse. Took 4 mg of actein and deoxyactein, added 10 ml of sterile double-distilled water to dissolve to a concentration of 0.4 mg/mL. 250 μL of distilled water for gavage for mice in the ConA model group; 250 μL of *Cimicifugae rhizoma* triterpenoid saponin extract obtained in Preparation Example 1 for gavage for mice in the triterpenoid saponin group, the dose was 15 mg/kg; 250 μL of the actein solution for gavage for mice in the carnitine group, the dose was 5 mg/kg; and 250 μL of deoxyactein solution for gavage for mice in the deoxyactein group, the dose was 5 mg/kg. Observed the 96-hour mortality rate of the animals.

The results are shown in FIG. 1. After 4-6 hours of ConA injection, the mice started to die, and the deaths were concentrated within 24 hours, after which the mortality rate decreased and stabilized at 48-96 hours. The survival rate of the ConA model group was 10%, and the survival rate of the mice increased after drug treatment. The survival rate of the triterpenoid saponin group was 70% (compared to the ConA model group, *, $p<0.001$). The survival rate of the actein group was 60% (compared with the ConA model group, , $p<0.01$), and the survival rate of the deoxyactein group was 40% (compared with the ConA model group, **, $p<0.01$). Survival rate was statistically analyzed by Kaplan-Meier, and the drug treatment groups had significant differences compared with the model group. The results indicate that *Cimicifugae rhizoma* triterpenoid saponin extract, actein, and deoxyactein all can improve the survival rate of mice with ConA acute hepatitis.

Experimental Example 2. Treatment Experiment for Liver Inflammation

The test materials and animals were the same as those in Experimental Example 1.

Grouping: C57BL/6 mice, male, 18-20 g, after 1 day of adaptive breeding, randomly divided into 5 groups: normal control group, ConA model group, triterpenoid saponin group, actein group and deoxyactein group.

Model preparation and drug administration: except the normal control group, mice were injected intravenously at a dose of ConA 15 mg/kg. The dosage of each group was the same as that of Experimental Example 1.

(1) The effects of drug administration in each group on serum ALT and AST of ConA mice were measured. Eight mice in each group were sacrificed under anesthesia 10 hours after ConA injection. Peripheral blood was taken, and serum was separated to detect ALT and AST.

(2) The effects of drug administration in each group on liver pathological damage in ConA mice were examined. Three mice in each group were sacrificed under anesthesia 10 hours after ConA injection. The left lobe of the liver was taken, cut into a size of about 5 mm3, and placed in 10% formalin solution, and dehydrated, transparently impregnated with wax, embedded, sliced, and spread, observed after staining;

(3) The effect of each group of drugs on serum cytokine secretion of ConA mice was examined. Six mice in each group. Peripheral blood was collected 3 hours after ConA injection and serum was separated to detect the secretion of cytokines TNF-α, IL-12, IL-6 and MCP-1. Serum was separated 10 hours after ConA injection to detect cell factor IFN-γ secretion.

Results (1): Effects of Drugs on Serum ALT and AST in Mice with ConA Hepatitis

The results are shown in Table 1. Compared with the normal group, the ALT and AST of the ConA model group were significantly increased (, $p<0.01$; *, $p<0.001$); the ALT and AST of each medication group were significantly decreased, which were significantly lower than those of ConA, and the differences were statistically significant (#, $p<0.05$; ##, $p<0.01$; ###, $p<0.001$). It indicates that *Cimicifugae rhizoma* triterpenoid saponin extract, actein, and deoxyactein can alleviate liver injury in ConA mice.

TABLE 1

Effect of Cimicifugae rhizoma Triterpenoid Saponin Extract, Actein, and Deoxyactein on Serum ALT and AST in ConA Hepatitis Mouse Model (MEAN ± SEM)

| | ALT(U/L) | AST(U/L) |
|---|---|---|
| Normal control group | 31.6 ± 2.7 | 89.3 ± 9.2 |
| ConA model group | 1465 ± 439.6** | 3150 ± 843.4*** |
| Cimicifugae rhizoma Triterpenoid Saponin extract group | 172.5 ± 72.9# | 273.5 ± 51.8### |
| Actein group | 39.8 ± 11.1### | 212 ± 33### |
| Deoxyactein group | 144.4 ± 68.5## | 390.8 ± 98.2## |

Note:
* represents a statistical difference between the ConA group and the normal control group,
***$p < 0.001$.
represents a statistically significant difference between the medication group and the ConA group,
$p < 0.05$;
$p < 0.01$;
$p < 0.001$.

Figure 2:
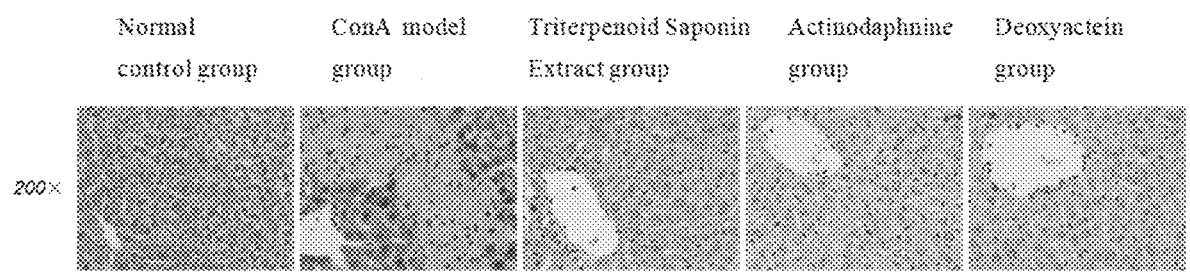
FIG. 2 is a micrograph of liver tissue of each model of mouse in Experimental Example 2 (HE staining)

Results (2): Effects of Drugs on Liver Pathological Damage in a Mouse Model of ConA Hepatitis The results are shown in FIG. 2. In the ConA model group, the liver cells of the mice were extensively degenerated, the structure of the liver lobules was disordered, the central veins of the hepatocytes were significantly dilated, the central veins and hepatic sinusoids were congested, and even large pieces of hepatocyte necrosis appeared. A large number of immune cell infiltrated; compared with the ConA group, the necrotic platelet of hepatocytes was significantly reduced in the *Cimicifugae rhizoma* triterpenoid saponin group, and a little leukocyte infiltration was seen; compared with the ConA group, large pieces of hepatocyte necrosis was significantly reduced and leukocyte infiltration was reduced in the actein group and the deoxyactein group.

Results (3): Effects of Drugs on Serum Cytokines in a Mouse Model of ConA Hepatitis The results are shown in Table 2. Compared with the normal group, the levels of TNF-α, IL-12, MCP-1, IL-6 and IFN-γ were significantly increased in the ConA model group, with statistical differences (***, $p<0.001$). Both triterpenoid saponin extract and actein significantly reduced the secretion levels of serum inflammatory factors IL-12, TNF-α, MCP-1, IL-6 and IFN-γ; deoxyactein significantly reduced IL-12, MCP-1, IL-6 and IFN-γ secretion levels (#, $p<0.05$; ##, $p<0.01$; ###, $p<0.001$).

final bovine type II collagen emulsion of a concentration of 1 mg/mL, and 0.1 mL was injected intradermally into each mouse. Took 4 mg of actein and deoxyactein, added 10 mL of sterile double-distilled water to dissolve, and prepared a mixed solution containing 0.4 mg/mL of actein and 0.4 mg/mL of deoxyactein for administration in the mice in Huangtuo group. 21 days after the primary immunization, the mice were immunized again for the secondary immunization. Starting from day 0 of the second immunization, 250 µL of distilled water was administered by gavage for mice in the CIA model group, and 250 µL of a mixed solution of actein and deoxyactein was administered by gavage for mice in the Huangtuo group, and the dose was 5 mg/kg. Gavage was given to the mice in each group daily, and mice were kept for 21 consecutive days.

Starting from day 0 of the secondary immunization, joint scores were evaluated every 3 days. Animals were scored using the joint scoring method (grade 0-4), and the assessment was based on the degree of joint redness and swelling and joint swelling and deformation. 0 point: no redness and swelling; 1 point: redness and swelling of the joint; 2 points: mild redness and swelling of the joint; 3 points: moderate

TABLE 2

Effects of Cimicifugae rhizoma Triterpenoid Saponin Extract, Actein, and Deoxyactein on Serum Inflammatory Cytokine Secretion in a Mouse Model of ConA (MEAN ± SEM)

| | IL-12 (pg/mL) | TNF-α (pg/mL) | MCP-1 (pg/mL) | IL-6 (pg/mL) | IFN-γ (pg/mL) |
|---|---|---|---|---|---|
| Normal control group | 7.3 ± 1.1 | 6.9 ± 0.7 | 21 ± 3.6 | 6.5 ± 2.1 | 3.3 ± 0.5 |
| ConA model group | 522.8 ± 99.3*** | 380 ± 42.6*** | 7835 ± 560.7*** | 4001 ± 465.7*** | 582.5 ± 77.7*** |
| Cimicifugae rhizoma Triterpenoid Saponin Extract group | 242.3 ± 42.6# | 253.7 ± 35.5# | 5871 ± 667.3# | 1970 ± 316.8## | 157.3 ± 33### |
| Actein group | 22 ± 1.9### | 173 ± 18.2## | 1832 ± 209.7### | 792 ± 48### | 116.2 ± 34.8### |
| Deoxyactein group | 190.5 ± 22.5## | 394.4 ± 41.8 | 4741 ± 665.7## | 1406 ± 134.1### | 245.3 ± 56## |

Note:
* represents statistical difference between the ConA group and the normal control group,
***$p < 0.001$.
# represents a statistical difference between the medication group and the ConA group,
$p < 0.05$;
$p < 0.01$;
$p < 0.001$.

Experimental Example 3. Effects of Combined Use of Actein and Deoxyactein on Arthritis Index in CIA Arthritis Mice Test materials: bovine type II collagen acetic acid solution and complete Freund's adjuvant were purchased from Chondrex company; isoferulic acid was purchased from Tianjin Yifang Technology Co., Ltd.

Animal: C57BL/6 mice, purchased from Beijing Huafukang Biotechnology Co., Ltd.

Grouping: 24 C57BL/6 mice, male, 18-20 g, after 1 day of adaptive breeding, randomly divided into 3 groups: normal group and CIA model group, 5 mice in each group; actein combined with deoxyactein group (Named below: Huangtuo group), 7 mice.

Model preparation and drug administration: prepared a 2 mg/mL bovine type II collagen acetic acid solution, took 2 mL of overnighted bovine type II collagen acetic acid solution, mixed thoroughly with 2 mL of complete Freund's adjuvant and emulsified (operation on ice), prepared the redness and swelling of the joint; 4 points: severe redness and swelling and dysfunction of the joint. Each limb was scored separately, and the sum of the scores of each limb was the arthritis index of the mouse. The highest score was 16 points. The higher the score, the more severe the joint symptoms.

The results are shown in Table 3. At 3 days after the second immunization, the CIA mice developed redness and mild swelling, with an average arthritis index of 0.57. As the course of the disease prolonged, the arthritis index gradually increased. By the 15th day, the ankle joints and toe joints were highly swollen, hyperemia appeared on the joint surface, and hind limbs could not bear weight. The average index of arthritis reached the plateau stage, which was 7.86±0.96. The average index of arthritis in the Huangtuo group was 3.71±1.17, which indicated that actein combined with deoxyactein significantly reduced the average arthritis index, and there is a significant difference compared with the CIA model group.

TABLE 3

Effects of combined use of actein and deoxyactein on arthritis index of CIA arthritis mice (MEAN ± SEM)

| | 0 day | 3 days | 6 days | 9 days | 12 days | 15 days |
|---|---|---|---|---|---|---|
| Normal group | 0 ± 0 | 0 ± 0 | 0 ± 0 | 0 ± 0 | 0 ± 0 | 0 ± 0 |
| CIA group | 0 ± 0 | 0.57 ± 0.28 | 2.71 ± 0.94 | 4.57 ± 0.9** | 7.43 ± 0.7*** | 7.86 ± 0.96*** |
| Huangtuo group | 0 ± 0 | 0.14 ± 0.13 | 0.14 ± 0.13# | 1.57 ± 0.85# | 2.71 ± 1.14## | 3.71 ± 1.17# |

Note:
* represents a statistical difference between the CIA group and the normal group,
**$p < 0.01$;
***$p < 0.001$.
represents a statistically significant difference between the medication group and the CIA group,
$p < 0.05$;
$p < 0.01$.

Figure 3:
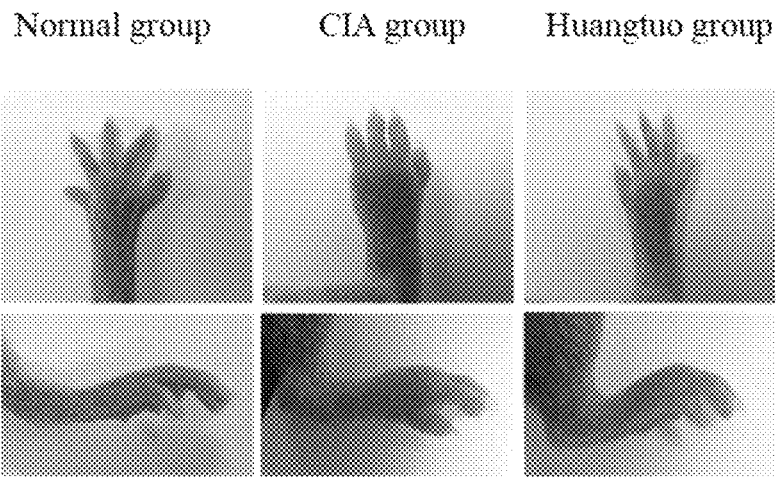
FIG. 3 shows pictures of anterior and posterior paw joints of mice in each group of Experimental Example 3.

FIG. 3 shows pictures of swelling of the paw joints of the CIA model mice and the treatment group on the 15th day. The pictures show that evident swelling of the ankle and toe joints of CIA arthritis mice, and the swelling of the mice in the Huangtuo group was significantly reduced. The results showed that combined use of actein and deoxyactein significantly improved joint redness and dysfunction in CIA arthritis mice.

Experimental Example 4. Effects of Combined Use of Actein and Deoxyactein on Body Weight of CIA Mice The test materials and animals were the same as those in Experimental Example 3.

Model preparation and drug administration: same as in Experimental Example 3. On the 21st day of secondary immunization in mice, they were weighed.

The results are shown in Table 4. There was no difference in the average weight of the mice among the groups. The results showed that the combination of actein and deoxyactein did not affect the body weight of CIA arthritis mice.

TABLE 4

Effects of combined use of actein and deoxyactein on body weight of CIA arthritis mice (MEAN ± SEM)

| | Weight (g) |
|---|---|
| Normal group | 21.96 ± 1.29 |
| CIA group | 21.51 ± 0.93 |
| Huangtuo group | 22.59 ± 0.64 |

Experimental Example 5. Effects of Combined Use of Actein and Deoxyactein on Organ Index of CIA Mice The test materials and animals were the same as those in Experimental Example 3.

Model preparation and drug administration: same as in Experimental Example 3. On the 21st day of secondary immunization of mice, they were sacrificed by anesthesia, and brain, heart, liver, spleen, lung, kidney, and testis were taken, weighed quickly, and organ index was evaluated.

The results are shown in Table 5. Compared with the CIA group, the average organ index of the Huangtuo group did not change. The results showed that the combination of actein and deoxyactein did not affect the organ index of CIA mice.

TABLE 5

Effects of actein and deoxyactein on organ index of CIA arthritis mice (MEAN ± SEM, unit mg)

| | Brain | Heart | Lung | Liver | Spleen | Kidney | Testis |
|---|---|---|---|---|---|---|---|
| Normal group | 383.0 ± 22.6 | 157.8 ± 6.7 | 149.5 ± 14.9 | 1330.7 ± 51.0 | 78.3 ± 3.6 | 343.0 ± 20.1 | 174.3 ± 6.7 |
| CIA group | 339.8 ± 6.6 | 149.8 ± 11.2 | 146.0 ± 10.2 | 1180.0 ± 86.3 | 164.2 ± 9.1 | 360.0 ± 17.3 | 169.0 ± 8.2 |
| Huangtuo group | 351.9 ± 5.2 | 150.1 ± 5.9 | 171.0 ± 10.2 | 1252.9 ± 20.6 | 180.7 ± 17.4 | 386.0 ± 11.3 | 160.9 ± 9.5 |

Experimental Example 6. Therapeutic Effect of Combination of Actein and Deoxyactein on CIA Arthritis Mice Test materials and animals: same as in Experimental Example 3. Anti-type II collagen antibody ELISA kit was purchased from Chondrex, Cytokine & Chemokine 36-Plex Mouse ProcartaPlex™ Panel 1A cytokine and chemokine detection kit was purchased from ThermoFisher.

Model preparation and drug administration: The dosage of each group was the same as that of Experimental Example 3. 21 days after the second immunization, the mice were anesthetized, and serum and limbs were taken.

(1) Micro-CT technology was used to detect the effect of each group on the joint structure of CIA mice. After taking 3 mice in each group, the right hind limbs were taken immediately after neck dissection and fixed 4% neutral formalin. After 2-3 days of fixation, a micro-CT scan was performed using a live animal imaging system. Extraction site: extracted the data of the area above the tibial plaque plate of the right hind limb of the mouse. Took 3 sets of data from each site. Size selection: the upper part of the tibial plaque plate (0.25*0.25*0.25); measurement indicators of the extracted bone: bone density, bone volume, bone volume fraction and number of bone trabeculae.

(2) The effect of each group on the serum anti-type II collagen antibody content of CIA mice was measured. Seven mice from each group, peripheral blood was collected and separated from serum. Anti-type II collagen antibody was detected by ELISA.

(3) The effects of each group on cytokine secretion in serum and joint tissues of CIA mice were examined. Seven mice from each group, peripheral blood was collected and separated from serum. Cytokines in serum were detected by multiple factors: IFN-γ, IL-6, IL-9, IL-12, IL-17A, IP-10, MCP-1, MCP-3. MIP-1α, MIP-1β, Eotaxin, and G-CSF; took the right hind limb knees, joints and paws and stored them in liquid nitrogen for quick freezing, homogenized and extracted protein. Multi-factor detection of cytokines in tissues: IL-9, IL-18 and MIP-2 secretion.

Results (1): The effect of Micro-CT technology on joint structure of CIA mice.

Figure 4:
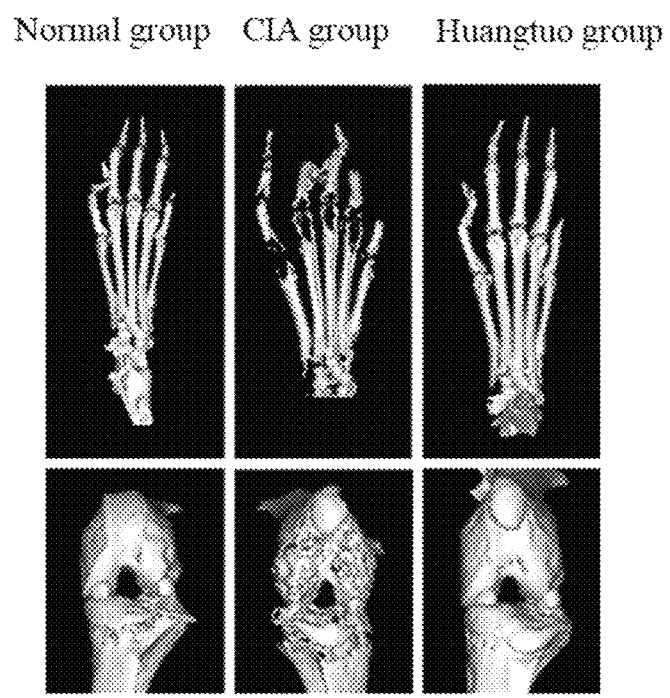
FIG. 4 is a Micro-CT image of the right hind limb knee joint, ankle joint, and toe joint of each group of Experimental Example 6.

The results are shown in FIG. 4. The ankle joint structure of the CIA model mice was blurry, osteoporosis and even severe damage were observed. The joint structure of the mice in the Huangtuo group remained almost intact, especially the bone destruction was significantly lighter than that of the model group. As shown in Table 6, compared with the normal group, the bone density, bone volume, bone volume fraction, and number of trabeculae of the mice in the CIA group decreased. Compared with the CIA model group, the bone measurement index of mice in the Huangtuo group significantly increased. The results show that the combination of actein and deoxyactein effectively relieved joint damage.

TABLE 6

Effects of combined use of actein and deoxyactein on bone damage in CIA arthritis mice (MEAN ± SEM)

| | Bone density | Bone volume | Bone volume fraction | Number of trabeculae (1/mm) |
|---|---|---|---|---|
| Normal group | 39.7 ± 9.8 | 0.0064 ± 0.0007 | 0.306 ± 0.060 | 7.113 ± 0.651 |
| CIA group | 4.1 ± 1.9** | 0.0002 ± 0.0001*** | 0.047 ± 0.032** | 0.977 ± 0.319*** |
| Huangtuo group | 30.6 ± 6.5## | 0.0043 ± 0.0015# | 0.170 ± 0.032# | 4.850 ± 0.974## |

Note:
* represents a statistical difference between the CIA group and the normal group,
**$p < 0.01$;
***$p < 0.001$.
represents a statistically significant difference between the medication group and the CIA group,
$p < 0.05$;
$p < 0.01$.

Result (2): Effect on serum anti-type II collagen antibody content in CIA mice.

The results are shown in Table 7. Compared with the normal group, the secretion of anti-type II collagen antibodies was significantly increased in the CIA group, with statistical differences (****, $p<0.0001$). The Huangtuo group had significantly reduced secretion of anti-type II collagen antibodies in the serum (####, $p<0.0001$). The results show that combined use of actein and deoxyactein reduced autoantibody secretion.

TABLE 7

Effects of combined use of actein and deoxyactein on serum anti-type II collagen antibodies in CIA arthritis mice (MEAN ± SEM)

| | Anti-type II collagen antibodies (Units/mL) |
|---|---|
| Normal group | 17 ± 2 |
| CIA group | 15797 ± 337*** |
| Huangtuo group | 7682 ± 3000### |

Note:
* indicates a statistical difference between the CIA group and the normal group,
***$p < 0.001$.
represents a statistically significant difference between the medication group and the CIA group,
$p < 0.001$.

Results (3): Effect on cytokine secretion in serum and joint tissues of CIA mice.

The results are shown in Table 8. Compared with the CIA group, the secretion levels of cytokines IFN-γ, IL-12, IL-17A, IL-6, IL-9, IL-18, chemokine MCP-1, and colony-stimulating factor G-CSF were significantly reduced, which were statistically different; at the same time, the secretion levels of IL-18 and MIP-2 in joint tissues were also significantly reduced, which were statistically different. The results showed that the combination of actein and deoxyactein significantly reduced the secretion levels of multiple cytokines, chemokines and colony-stimulating factors in serum and joint tissues and had a broad inhibitory effect on inflammation.

TABLE 8

Effects of combined use of actein and deoxyactein on cytokines in serum and joint tissues of CIA arthritis mice (MEAN ± SEM)

| | Normal group | CIA group | Huangtuo group |
|---|---|---|---|
| IFN-γ(pg/mL) | 15.4 ± 1.9 | 315.5 ± 36.2*** | 151.6 ± 22.2## |
| IL-12(pg/mL) | 19.2 ± 1.0 | 46.6 ± 7.0** | 22.8 ± 3.5# |

TABLE 8-continued

Effects of combined use of actein and deoxyactein on cytokines in serum and joint tissues of CIA arthritis mice (MEAN ± SEM)

| | Normal group | CIA group | Huangtuo group |
|---|---|---|---|
| IL-17A(pg/mL) | 2.5 ± 0.7 | 18.3 ± 2.1*** | 10.2 ± 1.8# |
| IL-6(pg/mL) | 2.4 ± 0.4 | 261.3 ± 40.2*** | 37.5 ± 9.3### |
| IL-18(pg/mL) | 30.5 ± 5.5 | 132.8 ± 26.1** | 46.2 ± 14.6# |
| IL-9(pg/mL) | 10.1 ± 1.9 | 34.7 ± 7.3* | 12.8 ± 1.2## |

TABLE 8-continued

Effects of combined use of actein and deoxyactein on cytokines in serum and joint tissues of CIA arthritis mice (MEAN ± SEM)

|  | Normal group | CIA group | Huangtuo group |
|---|---|---|---|
| MCP-1(pg/mL) | 42.0 ± 0.5 | 234.5 ± 4.1*** | 112.8 ± 10.1## |
| G-CSF(pg/mL) | 1.9 ± 0.2 | 44.6 ± 4.6*** | 8.2 ± 2.3### |
| Joint IL-18 (pg/mg) | 62.3 ± 14.1 | 325.3 ± 58.6* | 53.7 ± 10.3### |
| Joint MIP-2 (pg/mg) | 1.3 ± 0.3 | 391.4 ± 126.6* | 30.9 ± 13.7# |

Note:
*represents a statistical difference between the CIA group and the normal group,
*$p < 0.05$;
**$p < 0.01$;
***$p < 0.001$.
represents a statistically significant difference between the medication group and the CIA group,
$p < 0.05$;
$p < 0.01$;
$p < 0.001$.

Experimental Example 7. Effects of Combined Use of Actein and Deoxyactein on Granulocyte Proportion in CIA Arthritis Mice Test materials and animals: CD3-PerCP, NK1.1-APC antibody, Ki67-PE antibody, Intracellular Fixation & Permeabilization Buffer Set were purchased from eBioscience; B220-FITC antibody was purchased from BD Pharmingen; other required reagents Both are the same as Experimental Example 3.

Model preparation and administration: The dosage of each group was the same as that of Experimental Example 3.

Animal: C57BL/6 mice, purchased from Beijing Huafukang Biotechnology Co., Ltd.

Preparation of spleen single cell suspension: after anesthesia of C57BL/6 mice, separated the spleen of the mouse, placed the spleen in a small dish into which 4 mL of PBEB had been added, grinded the spleen with a matte surface of a glass slide, and filtered the spleen cells with 400 mesh into a flow tube, the supernatant was discarded after centrifugation. After adding 2 mL of RBC Lysis Buffer to lyse at room temperature for 15 minutes, the supernatant was discarded by centrifugation to harvest spleen cells. Then added 1 mL of PBS for resuspension, and repeatedly pipetting and mixing, and then pipetted 100 μL into the flow tube. Added anti-CD3, B220, and NK1.1 antibodies for surface staining. Incubated for 15 minutes in the dark, and then washed with 2 mL of PBEB. Centrifuged and discarded the supernatant. Performed intracellular staining.

Intracellular staining: 1) added 100 μL of Fixation Buffer Fixation Buffer, and protected the membrane from light at room temperature for 40 min; 2) added 1 mL of Permeabilization Buffer and washed twice, discarded the supernatant; 3) added 1 μL of Ki-67-PE antibody at room temperature and protected from light for 40 min; 4) the step was the same as 2); 5) intracellular Ki-67 expression in CD3$^-$NK1.1$^+$B220$^-$NK cells was detected by flow cytometry BD Calibar.

The results are shown in Table 9. Compared with normal mice, CIA arthritis mice showed an increased proportion of Ki-67$^+$ cells in NK cells in the spleen, indicating that NK cell proliferation activity was enhanced. The proportion of Ki-67$^+$ cells decreased with significant differences in the Huangtuo group, indicating that combined use of actein and deoxyactein inhibited NK cell proliferation.

TABLE 9

Effect of combination of actein and deoxyactein on NK cell proliferation in CIA arthritis mice (MEAN ± SEM)

|  | Proportino of Ki67$^+$cell ( % ) |
|---|---|
| Normal group | 16.4 ± 1.0 |
| CIA group | 48.9 ± 10.7* |
| Huangtuo group | 9.1 ± 1.1### |

Note:
*represents a statistical difference between the CIA group and the normal group,
*$p < 0.05$;
# represents a statistical difference between the medication group and the CIA group,
$p < 0.001$.

Experimental Example 8. Inhibitory Effect of Actein and Deoxyactein on Cytokines Secreted by Macrophages Test materials: LPS was purchased from Sigma; actein and deoxyactein were purchased from American ChromaDex; FBS was purchased from American PAA; DMEM high glucose medium; macrophage colony-stimulating factor (M-CSF) was purchased from PeproTech company; ELISA kit was purchased from BD company of the United States.

Animal: C57BL/6 mice, purchased from Beijing Huafukang Biotechnology Co., Ltd.

Isolation and culture of mouse bone marrow-derived macrophages (BMDM): after anesthesia of C57BL/6 mice, the mouses 2 pairs of femur and tibia were aseptically separated, and the bone marrow cells were flushed into a sterile flow tube using a 2 mL syringe with sterile PBS. Repeatedly pipetted into a bone marrow single cell suspension. After centrifugation, bone marrow cells were harvested, and 10 mL of complete medium containing 10% FBS, 1% glutamine, 1% double antibiotics (anti-penicillin, anti-streptomycin), and 10 ng/mL M-CSF were added to 100 mL mm cell culture dish to culture at 37° C. After 4 days, the above fresh medium was changed, and macrophages with large volume, adherent growth, and mature differentiation were observed under the microscope on the 7th day. The cells were scraped off with a cell scraper, and repeatedly blown and mixed to form a single cell suspension, and then seeded in a 96-well plate at $1 \times 10^5$ cells/well.

BMDM cells induced activation and drug treatment: BMDM cells were treated with different doses of actein and deoxyactein, and 100 ng/mL LPS was given to stimulate cells 1 h later to simulate the activation of macrophages by bacterial infection. The cell supernatant was collected 4 hours later, and cytokine secretion was detected by ELISA.

The results are shown in Table 10. LPS stimulated the activation of BMDM cells and expressed a large amount of inflammatory cytokines IL-12 and TNF-α. Actein significantly inhibited IL-12 secretion in the concentration range of 2.5 ng/mL to 312.5 ng/mL, and inhibited TNF-α secretion in the concentration range of 0.5 ng/mL to 312.5 ng/mL; deoxyactein significantly inhibited IL-12 secretion in a concentration range of 250 ng/mL to 500 ng/mL, and inhibited TNF-α secretion in a concentration range of 50 ng/mL to 500 ng/mL. The results showed that actein in a concentration range of 2.5 ng/mL to 312.5 ng/mL and deoxyactein in a concentration range of 250 ng/mL to 500 ng/mL both significantly inhibited macrophage activation.

TABLE 10

Actein and deoxyactein inhibited IL-12 and TNF-α secretion by macrophages (MEAN ± SEM)

|  | IL-12 (pg/mL) | TNF-α (pg/mL) |
| --- | --- | --- |
| Control group | 3.6 ± 0.9 | 10.9 ± 4 |
| LPS group | 226.6 ± 26.6*** | 2891 ± 57*** |
| Actein 0.5 ng/mL | 194.5 ± 22.3 | 2555 ± 62.3# |
| Actein 2.5 ng/mL | 136.3 ± 22.8# | 2483 ± 77.3# |
| Actein 12.5 ng/mL | 88.5 ± 10.6## | 2327 ± 77.3## |
| Actein 62.5 ng/mL | 48.2 ± 21.4# | 2056 ± 49.2### |
| Actein 312.5 ng/mL | 8 ± 0.8## | 2062 ± 49### |
| Deoxyactein 25 ng/mL | 244 ± 2.8 | 2529 ± 121.3 |
| Deoxyactein 50 ng/mL | 177.8 ± 12.5 | 2321 ± 97.4## |
| Deoxyactein 125 ng/mL | 142.3 ± 6.8 | 2440 ± 84.8# |
| Deoxyactein 250 ng/mL | 88.1 ± 22.3## | 2305 ± 76.8## |
| Deoxyactein 500 ng/mL | 42.2 ± 23.7## | 2077 ± 43.8## |

Note:
* represents a statistical difference between the LPS group and the blank group,
***$p < 0.001$.
represents a statistically significant difference between the medication group and the LPS group,
$p < 0.05$;
$p < 0.01$;
$p < 0.001$.

Experimental Example 9. Inhibitory Effect of Actein and Deoxyactein on IFN-γ Expression in NK Cells Test materials: CD45-PE, CD3-FITC, NK1.1-APC antibody, Intracellular Fixation & Permeabilization Buffer Set, and Cell Stimulation Cocktail were purchased from eBioscience.

Animal: C57BL/6 mice, purchased from Beijing Huafukang Biotechnology Co., Ltd.

Bone marrow single cell suspension preparation: after anesthesia of C57BL/6 mice, the 2 pairs of femur and tibia of the mouse were separated aseptically, the sterile bone marrow cells were pipetted into a sterile flow tube with a 2 mL syringe and sterile PBS to obtain bone marrow single cell suspension. After centrifugation, bone marrow cells were harvested, and 1.5 mL of complete medium containing 10% FBS, 1% glutamine, and 1% double antibiotics (anti-penicillin, anti-streptomycin) were added.

Intracellular staining after drug administration and NK cell induction activation: cells were treated with actein of intermediate concentration of 62.5 ng/mL and deoxyactein at a concentration of 250 ng/mL, and the cells were stimulated with Cell Stimulation Cocktail (containing PMA, ionomycin and protein transport inhibitors) for 5 h. Surface staining was performed with CD45-PE, CD3-FITC, NK1.1-APC antibodies, intracellular staining was performed with IL-12-APC antibodies, and the percentage of positive cells expressing IFN-γ in CD45+CD3−NK1.1+ NK cells was detected by flow cytometry.

The results are shown in Table 11. Under the stimulation of PMA+ionomycin, NK cells in the bone marrow were activated and showed a large amount of secretion of inflammatory cytokines IFN-γ. Compared with the group of PMA+ionomycin, actein and deoxyactein treatments significantly reduced the expression of IFN-γ and inhibited the activation of NK cells (*, $p<0.05$).

TABLE 11

Actein and deoxyactein inhibited IFN-γ expression in NK cells (MEAN ± SEM)

|  | IFN-γ+ (%) |
| --- | --- |
| Control group | 1.1 ± 0.2 |
| PMA + ionomycin group | 42.1 ± 2.7*** |
| Actein group | 33.0 ± 2.2# |
| Deoxyactein group | 29.5 ± 3.5# |

Note:
* represents a statistical difference between the PMA + ionomycin group and the blank group,
***$p < 0.001$.
represents a statistically significant difference between the medication group and the PMA + ionomycin group,
$p < 0.05$.

Experimental Example 10. Inhibitory Effect of Actein and Deoxyactein on IFN-γ Expression in NKT Cells Test material: same as Experimental Example 9.

Animal: C57BL/6 mice, purchased from Beijing Huafukang Biotechnology Co., Ltd

Bone marrow single cell suspension preparation: same as Experimental Example 9.

Drug treatment and intracellular staining after NKT cell induction activation: same as Experimental Example 9. Flow cytometry was used to detect the percentage of positive cells expressing IFN-γ in CD45+CD3+NK1.1+ NKT cells.

The results are shown in Table 12. Under the stimulation of PMA+ionomycin, NKT cells in bone marrow were activated, showing a large amount of secretion of inflammatory cytokines IFN-γ; compared with the group of PMA+ionomycin, actein and deoxyactein treatments significantly reduced the expression of IFN-γ and inhibited the activation of NKT cells (*, $p<0.05$; **, $p<0.01$).

TABLE 12

Actein and deoxyactein inhibited NKT cell expression of IFN-γ (MEAN ± SEM)

|  | IFN-γ+ (%) |
| --- | --- |
| Control group | 1.9 ± 0.2 |
| PMA + ionomycin group | 7.1 ± 0.7** |
| Actein group | 3.5 ± 0.6# |
| Deoxyactein group | 2.2 ± 0.4### |

Note:
* represents a statistical difference between the PMA + ionomycin group and the blank group,
**$p < 0.01$.
represents a statistically significant difference between the medication group and the PMA + ionomycin group,
$p < 0.05$;
$p < 0.01$.

Experimental Example 11. Inhibitory Effect of Actein and Deoxyactein on T Lymphocytes Expressing IFN-γ

Test materials: CD3-PE antibodies were purchased from BD Company in the United States, and CD4-FITC and CD8-PerCP antibodies were purchased from eBioscience Company; the remaining required reagents were the same as those in Experimental Example 9.

Animal: C57BL/6 mice, purchased from Beijing Huafukang Biotechnology Co., Ltd.

Preparation of spleen single cell suspension: after anesthesia of C57BL/6 mice, isolated the spleen of the mouse, placed the spleen in a sterile petri dish with 4 mL of PBEB added, grinded the spleen with a glass frosted surface, and filtered with a sterile 400 mesh filter. The spleen cells were placed in a flow tube, and the supernatant was discarded after centrifugation. After adding 2 mL of RBC Lysis Buffer to lyse at room temperature for 15 minutes, the supernatant was discarded by centrifugation to harvest the spleen cells. Then added 1.5 mL of complete medium containing 10% FBS, 1% glutamine, and 1% double antibiotics (anti-penicillin, anti-streptomycin), and mixed well by repeated pipetting.

Drug treatment and intracellular staining after T cell induction activation: cells were treated with 62.5 ng/mL actein and 250 ng/mL deoxyactein in a medium concentration, and Cell Stimulation Cocktail (containing PMA, ionomycin and protein transport inhibitor) was added to stimulate the cells for 5 h. Flow cytometry was used to detect the percentage of positive cells expressing IFN-γ in $CD3^+CD4^+$ T cells and the percentage of positive cells expressing IFN-γ in $CD3^+CD8^+$ T cells.

Results: as shown in Table 13, $CD4^+$ T cells and $CD8^+$ T expressed a large amount of inflammatory cytokines IFN-γ under the stimulation of PMA+ionomycin; compared with PMA+ionomycin group, actein or deoxyactein alone did not reduce the expression of IFN-γ, but the combination of the two had a synergistic effect and significantly reduced the expression of IFN-γ (, $p<0.01$; *, $p<0.001$).

TABLE 13

Actein and deoxyactein inhibited T-lymphocyte expression of IFN-γ (MEAN ± SEM)

| | IFN-γ+ (%) | |
| --- | --- | --- |
| | $CD4^+$T cell | $CD8^+$T cell |
| PBS group | 0.4 ± 0.1 | 0.3 ± 0.04 |
| PMA + ionomycin group | 3.8 ± 0.6** | 14.5 ± 1.0*** |
| Actein group | 3.1 ± 0.6 | 14.3 ± 0.7 |
| Deoxyactein group | 2.0 ± 0.7 | 12.1 ± 1.3 |
| Actein and deoxyactein combined group | 0.9 ± 0.1## | 5.4 ± 0.5### |

Note:
* represents a statistical difference between the PMA + ionomycin group and the blank group,
**$p < 0.01$;
***$p < 0.001$.
represents a statistically significant difference between the medication group and the PMA + ionomycin group,
$p < 0.01$;
$p < 0.001$.

In summary, *Cimicifugae rhizoma* triterpenoid saponin extract, actein, and deoxyactein significantly improved the survival rate of the mouse model of hepatitis, improved the level of liver function, reduced liver pathological damage, and inhibited the release of inflammatory factors, and had a significant liver protection effect.

The combination of actein and deoxyactein significantly reduced the average index of arthritis in mouse models of arthritis, improved bone structure, reduced bone erosion, inhibited the release of inflammatory factors, inhibited NK cell proliferation, and had significant immune regulation and joint protection effects.

In addition, *Cimicifugae rhizoma* triterpenoid saponin extract and its main components actein and deoxyactein also showed significant anti-inflammatory effects, and inhibited the activation of macrophages, NK and NKT cells, and the synergistic effects of the two also inhibited T lymphocytes activation and have a wide range of immunosuppressive effects.

Unless specifically defined, the terms used in the present invention have the meanings generally understood by those skilled in the art.

The embodiments described in the present invention are for exemplary purposes only and are not intended to limit the protection scope of the present invention. Those skilled in the art can make various other substitutions, changes, and improvements within the scope of the present invention. Therefore, the present invention is not It is limited to the above-mentioned embodiment and is only limited by the claims.

What is claimed is:

1. A pharmaceutical composition consisting of isolated actein and deoxyactein as active ingredients; wherein the mass ratio of actein and deoxyactein is from 1:5 to 5:1.

2. The pharmaceutical composition according to claim 1, wherein the mass ratio of actein and deoxyactein is from 1:3 to 3:1.

3. The pharmaceutical composition according to claim 2, wherein the mass ratio of actein and deoxyactein is 1:1.

* * * * *